United States Patent [19]
Axelsson et al.

[11] Patent Number: 5,441,969
[45] Date of Patent: Aug. 15, 1995

[54] IMIDAZOLE COMPOUNDS, THEIR PREPARATION AND USE

[75] Inventors: Oskar Axelsson; Dan Peters, both of Malmö, Sweden; Elsebet O Nielsen, Copenhagen, Denmark

[73] Assignee: NeuroSearch A/S, Glostrup, Denmark

[21] Appl. No.: 172,427

[22] Filed: Dec. 22, 1993

[30] Foreign Application Priority Data

Dec. 23, 1992 [DK] Denmark .................. 1540/92

[51] Int. Cl.$^6$ .................. A61K 31/445; C07D 235/30
[52] U.S. Cl. .................. 514/338; 514/365; 514/388; 546/271; 548/135; 548/181; 548/304.7; 548/305.4; 548/306.1; 548/307.4
[58] Field of Search .................. 548/181, 304.7, 305.4, 548/306.1, 307.4, 135; 514/388, 365, 338; 546/271

[56] References Cited

U.S. PATENT DOCUMENTS 5,196,444  3/1993  Nakh .................. 514/381
5,210,091  5/1993  Adelsson .................. 514/322

FOREIGN PATENT DOCUMENTS 392317  10/1990  European Pat. Off. .................. 514/325

OTHER PUBLICATIONS

J. Med. Chem., 33, pp. 1312–1336 (1990).
J. Med. Chem., 34, pp. 2919–2922 (1991).

Primary Examiner—Robert Gerstl
Attorney, Agent, or Firm—Gordon W. Hueschen

[57] ABSTRACT

The present invention discloses compounds of the formula

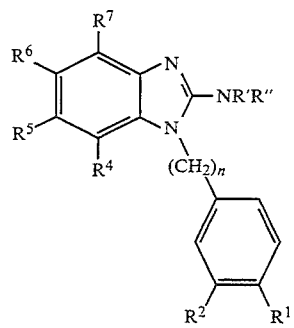

or a pharmaceutically-acceptable addition salt thereof wherein $R'$ and $R''$ independently of each other are hydrogen or alkyl, or $R'$ and $R''$ together form a 3 to 6 membered alkylene chain;

one of $R^1$ and $R^2$ is aryl which may be substituted one or more times with halogen, $CF_3$, CN, OH, alkyl, cycloalkylalkyl, alkenyl, alkynyl, alkoxy, amino, nitro, sulphamoyl, tetrazolyl, $CO_2H$, $CO_2$-alkyl and the other of $R^1$ and $R^2$ is hydrogen, halogen, alkoxy, amino or alkyl; and $R^4$, $R^5$, $R^6$ and $R^7$ independently of each other are hydrogen, halogen, amino, nitro, CN, OH, $CF_3$, alkyl or alkoxy; and n is 0 or 1; provided that neither of $R^1$ and $R^2$ is phenyl or substituted phenyl when n is 0.

The compounds are useful as pharmaceuticals, for example, in the treatment of ischemia, anoxia, migraine and psychosis.

12 Claims, No Drawings

IMIDAZOLE COMPOUNDS, THEIR PREPARATION AND USE

The present invention relates to therapeutical active compounds and their use as well as to pharmaceutical preparations comprising the compounds. The compounds of the invention possess valuable activity as calcium channel blockers which make them useful in the treatment of anoxia, ischemia, psychosis and migraine for example.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the Central Nervous System (CNS) is known to cause most of the degenerative changes connected with the above diseases. Therefore compounds which can block the calcium channels of brain cells will be useful in the treatment of anoxia, ischemia, migraine, epilepsia and in the prevention of the degenerative changes connected with the same.

Compounds blocking the so called L-type calcium channels in the CNS will be useful for the treatment of the above disorders by directly blocking the calcium uptake in the CNS.

Further, it is well known that the so called N- and P-types of calcium channels, as well as possibly other types of calcium channels, are involved in the regulation of neurotransmitter release. Compounds blocking the N- and/or P-types of calcium channels will indirectly and very powerfully prevent calcium overload in the CNS after the hyperactivity periods of the brain as described above by inhibiting the enhanced neurotransmitter release seen after such hyperactivity periods of the CNS, and especially the neurotoxic enhanced neurotransmitter, glutamate, release after such hyperactivity periods of the CNS. Furthermore, blockers of the N- and/or P-types of calcium channels will as dependent upon the selectivity of the compound in question inhibit the release of various other neurotransmitters such as aspartate, GABA, glycine, dopamine, serotonin and noradrenaline. Therefore blockers of N- and/or P-types of calcium channels, as well as of possibly other types of calcium channels, may be useful in the treatment of psychosis, Parkinsonism, depression, epilepsia and other convulsive disorders.

It is an object of the present invention to provide compounds capable of blocking the L-type and/or the N-type and/or the P-type of calcium channels, and/or other types of calcium channels.

The invention then, inter alia, comprises the following, alone or in combination.

A method of treating a disorder, which is responsive to the partial or complete blockade of calcium channels of the central nervous system of a living animal body, including a human, which comprises administering to such a living animal body, including a human, in need thereof a therapeutically-effective amount of a compound selected from those having the formula:

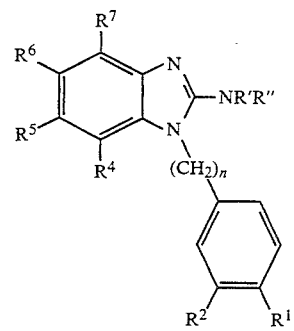

or a pharmaceutically-acceptable addition salt thereof wherein

R' and R" independently of each other are hydrogen or alkyl, or R' and R" together form a 3 to 6 membered alkylene chain;

one of $R^1$ and $R^2$ is aryl which may be substituted one or more times with halogen, $CF_3$, CN, OH, alkyl, cycloalkylalkyl, alkenyl, alkynyl, alkoxy, amino, nitro, sulphamoyl, tetrazolyl, $CO_2H$, $CO_2$-alkyl and the other of $R^1$ and $R^2$ is hydrogen, halogen, alkoxy, amino or alkyl; and $R^4$, $R^5$, $R^6$ and $R^7$ independently of each other are hydrogen, halogen, amino, nitro, CN, OH, $CF_3$, alkyl or alkoxy; and n is 0 or 1; provided that neither of $R^1$ and $R^2$ is phenyl or substituted phenyl when n is 0, and a method as above, wherein stroke, anoxia, ischemia, migraine, or epilepsy is treated, and a method as above, wherein psychosis, Parkinsonism, depression, epilepsy or any other convulsive disorder is treated, and a method as any above, wherein the compound employed is 2-Amino-1-[3-(4-methoxy-1,2,5-thiadiazol-3-yl)-phenyl]-benzimidazole,
1,3-bis(2-amino-1-benzimidazolyl)benzene,
2-Amino-1-[3-(3-formyl-4-thienyl)-phenyl]-benzimidazole,
2-Amino-1-[3-(3-hydroxymethyl-4-thienyl)-phenyl]-benzimidazole,
2-Amino-1-[3(2-thiazolyl)phenyl]benzimidazole,
2-Amino-1-[3(2-thienyl)phenyl]-5-trifluoromethyl-benzimidazole,
2-Amino-1-(4-phenylbenzyl)-5-trifluoromethylbenzimidazole,
2-Amino-1-[6-(2-hydroxypyridyl)phenyl]benzimidazole hydrochloride,
2-Amino-1-[3(2-thiazolyl)phenyl]benzimidazole,
2-Amino-1-[3-(2-furyl)phenyl]benzimidazole oxalate,
2-Amino-1-[4-(2-furyl)phenyl]benzimidazole,
2-Amino-1-[3-(2-thienyl)phenyl]benzimidazole,
2-Amino-1-[3-(3-methoxymethyl-2-furyl)phenyl]benzimidazole,
2-Amino-1-[3-(1,3,5-trimethyl-4-pyrazolyl)phenyl]-benzimidazole,
2-Amino-1-[3-(3-methoxymethyl-2-furyl)-4-methylphenyl]benzimidazole,
2-Amino-1-[3-(2-furyl)-4-methylphenyl]benzimidazole,
1-(2-Amino-1-benzimidazolyl)-3-(1-benzimidazolyl)-benzene hydrochloride,
2-Amino-1-[3-(5-acetamido-1-methyl-4-pyrazolyl)-phenyl]benzimidazole, 2-Amino-1-[3-(5-amino-1-methyl-4-pyrazolyl)-phenyl]benzimidazole hydrochloride,
2-Amino-1-[3-(3-furyl)-4-cyanophenyl]benzimidazole,
2-Amino-1-[3-(2-furyl)-4-methoxyphenyl]benzimidazole,
2-Amino-1-[3-(2-furyl)-4-dimethylaminophenyl]benzimidazole,
2-Amino-1-[3-(5-[2H- 1,3-benzodioxol])phenyl]benzimidazole,
2-Amino-1-[3-(5-indolyl)phenyl]benzimidazole, or
1,3-Bis(2-amino-1-benzimidazolyl)benzene,
or a pharmaceutically-acceptable addition salt thereof, and the method as first above, wherein the active ingredient is administered in form of a pharmaceutical composition thereof, in which it is present together with a pharmaceutically-acceptable carrier of diluent, and a method of preventing the degenerative changes connected with stroke, anoxia, ischemia, migraine, Parkinsonism, epilepsy or any other convulsive disorder, which comprises administering to a living animal body, including a human, in need thereof a therapeutically-effective amount of a compound as first above, and a compound having the formula

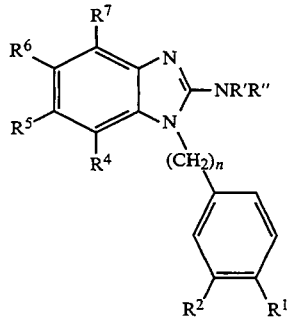

or a pharmaceutically-acceptable addition salt thereof wherein

R' and R" independently of each other are hydrogen or alkyl, or R' and R" together form a 3 to 6 membered alkylene chain;

one of $R^1$ and $R^2$ is aryl which may be substituted one or more times with halogen, $CF_3$, CN, OH, alkyl, cycloalkylalkyl, alkenyl, alkynyl, alkoxy, amino, nitro, sulphamoyl, tetrazolyl, $CO_2H$, $CO_2$-alkyl and the other of $R^1$ and $R^2$ is hydrogen, halogen, alkoxy, amino or alkyl; and $R^4$, $R^5$, $R^6$ and $R^7$ independently of each other are hydrogen, halogen, amino, nitro, CN, OH, $CF_3$, alkyl or alkoxy; and n is 0 or 1; provided that neither of $R^1$ and $R^2$ is phenyl or substituted phenyl when n is 0, and a compound as above which is
2-Amino-1-[3-(4-methoxy-1,2,5-thiadiazol-3-yl)-phenyl]-benzimidazole,
1,3-bis(2-amino-1 -benzimidazolyl)benzene,
2-Amino-1-[3-(3-formyl-4-thienyl)-phenyl]-benzimidazole,
2-Amino-1-[3-(3-hydroxymethyl-4-thienyl)-phenyl]-benzimidazole,
2-Amino-1-[3(2-thiazolyl)phenyl]benzimidazole,
2-Amino-1-[3(2-thienyl)phenyl]-5-trifluoromethyl-benzimidazole,
2-Amino-1-(4-phenylbenzyl)-5-trifluoromethylbenzimidazole, 2-Amino-1-[6-(2-hydroxypyridyl)phenyl]benzimidazole hydrochloride,
2-Amino-1-[3(2-thiazolyl)phenyl]benzimidazole,
2-Amino-1-[3-(2-furyl)phenyl]benzimidazole oxalate,
2-Amino-1-[4-(2-furyl)phenyl]benzimidazole,
2-Amino-1-[3-(2-thienyl)phenyl]benzimidazole,
2-Amino-1-[3-(3-methoxymethyl-2-furyl)phenyl]benzimidazole,
2-Amino-1-[3-(1,3,5-trimethyl-4-pyrazolyl)phenyl]-benzimidazole,
2-Amino-1-[3-(3-methoxymethyl-2-furyl)-4-methylphenyl]benzimidazole,
2-Amino-1-[3- (2-furyl)-4-methylphenyl]benzimidazole,
1-(2-Amino-1-benzimidazolyl)-3-( 1 -benzimidazolyl)-benzene hydrochloride,
2-Amino-1-[3-(5-acetamido-1-methyl-4-pyrazolyl)-phenyl]benzimidazole,
2-Amino-1-[3-(5-amino-1-methyl-4-pyrazolyl)-phenyl]benzimidazole hydrochloride,
2-Amino-1-[3-(3-furyl)-4-cyanophenyl]benzimidazole,
2-Amino-1-[3-(2-furyl)-4-methoxyphenyl]benzimidazole,
2-Amino-1-[3-(2-furyl)-4-dimethylaminophenyl]benzimidazole,
2-Amino-1-[3-(5-[2H- 1,3-benzodioxol])phenyl]benzimidazole,
2-Amino-1-[3-(5-indolyl)phenyl]benzimidazole, or
1,3-Bis(2-amino-1-benzimidazolyl)benzene,
or a pharmaceutically-acceptable addition salt thereof, and a pharmaceutical composition comprising an effective amount of a compound as any above, or a pharmaceutically-acceptable addition salt thereof, together with at least one pharmaceutically-acceptable carrier or diluent.

Halogen is fluorine, chlorine, bromine, or iodine.

Alkyl means a straight chained or branched chain of from one to six carbon atoms or cyclic alkyl (cycloalkyl) of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Alkenyl means a group from two to six carbon atoms, including one double bond, for example, but not limited to ethylene, 1,2- or 2,3-propylene, 1,2-, 2,3-, or 3,4-butylene.

Alkynyl means a group from two to six carbon atoms, including one triple bond, for example, but not limited to ethynyl, 2,3-propynyl, 2,3- or 3,4-butynyl.

Cycloalkylalkyl means cycloalkyl as above and alkyl as above, meaning for example, cyclopropylmethyl.

Alkoxy is O-alkyl, wherein alkyl is as defined above.

Amino is $NH_2$ or NH-alkyl or N-(alkyl)$_2$, wherein alkyl is as defined above.

Sulphamoyl is $SO_2$-amino.

Aryl is a 5- or 6-membered monocyclic heterocyclic group or a bicyclic heterocyclic group. Such an aryl group includes, for example, oxazol-2-yl, oxazol-4-yl, oxazol-5-yl, isoxazol-3-yl, isoxazol-4-yl, isoxazol-5-yl, thiazol-2-yl, thiazol- 4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol3-yl, 1,2,5-oxadiazol-4-yl, 1,2,5-thiadiazol-3-yl, 1,2,5-thiadiazol-4-yl, 2-imidazolyl, 4-imidazolyl, 2-pyrrolyl, 3-pyrrolyl, 2-furanyl, 3-furanyl, 2-thienyl, 3-thienyl, 2-pyridyl, 3-pyridyl, 4-pyridyl, benzimidazolyl, indolyl.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate for example.

Other acids such as oxalic acid, while not in themselves pharmaceutically acceptable may be useful in the preparation of salts useful as intermediates in obtaining compounds of the invention and their pharmaceutically acceptable acid addition salts.

Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Starting materials for the processes described in the present application are known or can be prepared by known processes from commercially available chemicals.

The products of the reactions described herein are isolated by conventional means such as extraction, crystallization, distillation, chromatography, and the like.

It has been found that the selectivity for the calcium channels, is dependent upon the degree of coplanarity of the aryl group with the phenyl ring to which it is attached, and it has been found that the selectivity and affinity for the blockade of the calcium channels can be regulated by regulating the degree of the coplanarity of the aryl ring with the phenyl ring to which it is attached. The degree of this coplanarity is very sensitive to the Substitution of the aryl ring, especially in the ortho position to the attachment atom to the phenyl ring. The degree of the coplanarity is thus suitably regulated by way of substituting the aryl ring of a compound as above. Suitable substituted aryl groups are, for example, 4-alkoxy-oxazol-5-yl, 4-alkoxy-1, 2,5-thiadiazol-3-yl, for example.

The compounds can be prepared by conventional methods well known in the art.

Such methods include for example a) the step of reacting a compound having the formula

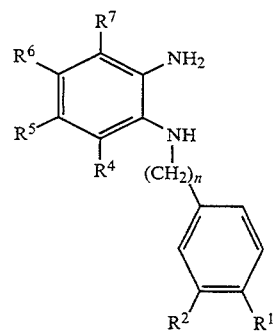

wherein n, $R^1$, $R^2$, $R^4$, $R^5$, $R^6$ and $R^7$ have the meanings set forth above, with BrCN to form a compound of the invention, and if the 2-amino group of the end product is intended to be alkyl substituted, then by a following alkylation with the relevant alkylhalogenide or another suitable alkylating reagent, or b) the step of reacting a compound having the formula

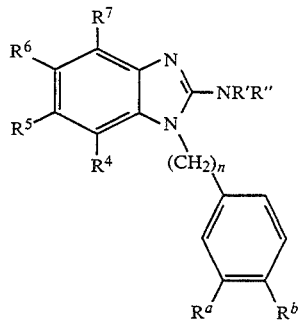

wherein one of $R^a$ or $R^b$ is halogen, and the other of $R^a$ or $R^b$ is $R^2$ and $R^1$ respectively, and n, R', R", $R^4$, $R^5$, $R^6$ and $R^7$ each have the meanings set forth above, with Aryl-boronic acid, an Aryl-boronic acid ester, or an Aryl-trialkylstannyl compound in a tetrakis(triphenylphosphine)palladium(O) catalyzed reaction, or c) the step of reacting a compound having the formula

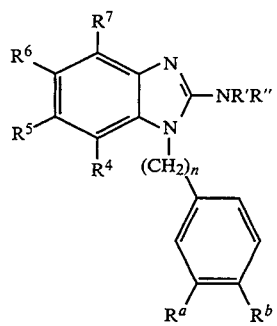

wherein one of $R^a$ or $R^b$ is $B(OH)_2$, 1,3,2-dioxaborinanyl, or trialkylstannyl, and the other of $R^a$ or $R^b$ is $R^2$ and $R^1$ respectively, and n, R', R'', $R^4$, $R^5$, $R^6$ and $R^7$ each have the meanings set forth above, with Arylhalogenide in a tetrakis (triphenylphosphine)palladium(O) catalyzed reaction.

The starting compounds are well known compounds, either as commercial available compounds, or easily available according published literature.

Biology

A high influx of calcium from extracelluar compartments into neurons is seen after opening of voltage operated calcium channels. Such opening of calcium channels may be induced by depolarization of neuronal membranes.

A crude synaptosome preparation contains small vesicles surrounded by neuronal membranes, and it is possible to study an opening of the voltage operated calcium channels in such a preparation.

In the below described test influx of $^{45}Ca$ into rat synaptosomes is studied under , depolarized conditions. The effect of test substances on the depolarization induced calcium uptake can thus be studied.

The calcium influx measured in this test is believed to represent the P- and L-type of calcium channels and compounds believed to block both the P- and the L-type of calcium channels will often exhibit a bifasic dose/response curve. The compounds of the present invention which potently block the calcium influx of up to 20 to 40% in this test are believed to be blockers of predominantly the P-type of calcium channels and the compounds of the present invention, which at somewhat higher concentrations block the calcium influx more completely or totally, are believed to be both P- and L-type calcium channel blockers, or predominantly L-type of calcium channel blockers.

Test Procedure

The cerebral cortex from a male Wistar rat is homogenized in 20 ml ice cold 0.32M. saccharose. In the following steps the temperature is kept at 0° C. to 4° C. The homogenate is centrifuged at 1,000×g for 10 minutes and the supernatant recentrifuged for 20 minutes at 18,000×g. The obtained pellet is resuspended in 0.32M saccharose (10 ml per. g of original tissue).

Aliquots of 0.05 ml of the hereby obtained synaptosome suspension are added to glass tubes containing 0.625 ml of a NaCl buffer (136 mM NaCl, 4 mM KCl, 0.35 mM $CaCl_2$, 1.2 mM $MgCl_2$, 20 mM Tris HCl, 12 mM glucose, pH 7.4) as well as 0.025 ml of different test substances in 48% ethanol. These tubes are pre- incubated for 30 minutes on ice and thereafter for 6 minutes at 37° C.

$^{45}Ca$ uptake is initiated by addition to above glasstubes of 0.4 ml $^{45}CACl_2$ (specific activity: 29-39 Ci/g; 0.5 Ci per tube). For depolarized samples the 0.4 ml $^{45}CACl_2$ contain KCl (145 mM) and for non-depolarized NaCl (145 mM). The samples are incubated for 15 seconds.

The $^{45}Ca$ uptake is stopped by filtering through glass fibre filters, which am subsequently washed 3 times with an ice cold solution of 145 mM KCl, 7 mM EGTA and 20 mM Tris HCl, pH 7.4 (5.0 ml). The radioactivity on the filters are measured by liquid scintillation spectrometry. Experiments are performed in duplicate.

Sample Preparation

Above test substances are dissolved in, for example, 10 ml 48% ethanol at a concentration of 0.44 mg/ml. Dilutions are made in ethanol. Test substances are tested at concentrations of 0.1, 0.3, 1, 3, 10 .. μg/ml.

Results

Generally the compounds of the present invention in a low micromolar range (0.5 to 2 μM) block 20 to 40% of the calcium influx measured in the above described test. Other compounds of the present invention also show the characteristics of L-type calcium channel blocking properties at somewhat higher concentrations.

It has been found (electrophysiological studies using the patch-clamp technique as described by Hamill et al., Pflügers Arch. 391, 85-100 (1981)), that compounds of the invention block the N-type of calcium channels in a low micromolar range (1 to 20 μM). A very potent compound is 2-Amino-1-[3-(4-methoxy-1,2,5-thiadiazol-3-yl)phenyl]-benzimidazole. Some compounds of the invention also block the L-type calcium channels.

Therefore the compounds are useful in the treatment of anoxia, ischemia and migraine (see also WO 91/07980).

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefor and, optionally, other therapeutic and-/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing one (1) milligram of active ingredient or, more broadly, 0.01 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, sollubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

Due to the high degree of activity, the compounds of the invention may be administered to a subject, e.g., a living animal body, in need of alleviation, treatment, or amelioration of a disorder which is responsive to the activity or influence of the compounds of the present invention including responsive to the Ca channel blocking properties of the compounds of the invention. The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether oral, rectal, or parenteral (including subcutaneous) route, in an effective amount. Suitable dosage ranges are 1–500 milligrams daily, preferably 1–100 milligrams daily, and especially 1–30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further; however they are not to be construed as limiting.

EXAMPLE 1

Method A. 1-[6-(-2-methoxyoxpyridyl)phenyl]-2-aminobenzimidazole oxalate

A mixture of 3-(2-amino-1-benzimidazolyl)-phenyl-1,3,2-dioxaborinane (3.2 g, 10.9 mmol), 2-bromo-6-methoxy pyridine (0.38 g, 0.33 mmol), tetrakis(triphenylphosphine)palladium(O) (0.29 g, 0.25 mmol), 1M aqueous NaHCO$_3$ (5.5 ml, 5.5 mmol), and ethylene glycol dimethyl ether (110 ml) was refluxed under nitrogen for 4 h. After cooling to room temperature, ethyl acetate (200 ml) was added and the phases were separated. The organic phase was washed with water (2×40 ml) and dried over magnesium sulfate. The corresponding oxalate was precipitated from ether. Yield: 1.79 g, 49%, mp. 110°–112° C.

EXAMPLE 2

Method B. 2-Amino-1-[3-(3-formyl-4-thienyl)-phenyl]-benzimidazole

A mixture of 2-amino-1-(3-iodophenyl)-benzimidazole (2.50 g, 7.46 mmol), 4-formyl-3-thienylboronic acid (1.39 g, 8.95 mmol), tetrakis(triphenylphosphine)palladium(O) (0.26 g, 0.22 mmol), 1 M aqueous NaHCO$_3$ (37 ml, 37 mmol), and ethylene glycol dimethyl ether (70 ml) was refluxed under nitrogen for 4 h. After cooling to room temperature, ethyl acetate (200 ml) was added and the phases were separated. The organic phase was washed with water (2×40 ml). After evaporation of the solvent the product was purified by chromatography on silica gel with dichloromethane +10% methanol as the eluent. After removal of the solvent, the product was obtained as an off white solid. Yield 1.5 g, 63%, dec. at ≈120° C.

2-Amino-1-[3-(4-methoxy-1,2,5-thiadiazol-3-yl)-phenyl]-benzimidazole oxalate was synthesized according to method B with 3-chloro-4-methoxy-1,2,5-thiadiazole as Starting material. Yield: 54%, mp. 130°–132′C.

EXAMPLE 3

2-Amino-1-[3-(3-hydroxymethyl-4-thienyl)-phenyl]-benzimidazole was synthesized as above with amino-1-(3-iodophenyl)-benzimidazole and 4-hydroxymethyl-3-thienylboronic acid as starting materials. Yield 56%, mp. 106°–108° C.

EXAMPLE 4

METHOD C. 2-Amino-1-[3(2-thiazolyl)phenyl]benzimidazole.

A mixture of 1-(2-amino-1-benzimidazolyl)-3-iodobenzene (4 g, 11.9 mmol), 2-trimethylstannylthiazole (8.9 g, 23.8 mmol), and bis(triphenylphosphine)palladium dichloride (0.42 g, 0.60 mmol) in DMF (10 ml) was heated to 100° C. and stirred under nitrogen for 12 hours. Aqueous workup (EtOAc) gave, after evaporation, a crystalline product. Yield 2.5 g, 72% mp 224°–226° C. In certain cases the product was further purified by column chromatography or by precipitation of the product as a salt.

EXAMPLE 5

METHOD D. 2-Amino-1-(3-iodophenyl)-benzimidazole.

A mixture of 2-amino-3′-iodo-diphenylamine (62.0 g, 200 mmol), cyanogen bromide (38.1 g, 360 mmol) and DMF(600 ml) was stirred in a sealed bottle in the absence of light for one week.

Water (800 ml) was added and the resulting solution was filtered and washed with ether (3×100 ml). The aqueous phase was taken to pH 9 by the addition of a 2 M aqueous sodium hydroxide solution. The crystalline product was filtered off and dried. Yield: 52.2 g, 78%, mp. 194°–196′C.

EXAMPLE 6

2-Amino-1-]3(2-thienyl)phenyl]-5-trifluoromethyl-benzimidazole was prepared from 1-(2-amino-5-trifluoromethyl-1-benzimidazolyl)-3-iodobenzene and 2-thienylboronic acid according method B. mp 89°–91° C.

EXAMPLE 7

2-Amine-1-(4-phenylbenzyl)-5-trifluoromethylbenzimidazole was prepared from N-phenylbenzyl-4-trifluoromethyl-ortho-phenylenediamine according to method D. mp 264°–266° C.

EXAMPLE 8

2-Amino-1-[6-(2-hydroxypyridyl)phenyl]benzimidazole hydrochloride was prepared from 2-amino-1-[6-(2-methoxypyridyl)phenyl]benzimidazole by refluxing in 25% aqueous hydrochloric acid. mp 215°–217° C.

EXAMPLE 9

2-Amino-1-[3(2-thiazolyl)phenyl]benzimidazole was prepared from 1-(2-amino-1-benzimidazolyl)-3-iodobenzene and 2-trimethylstannylthiazole by method C. mp 224°–226° C.

EXAMPLE 10

2-Amino-1-[3-(2-furyl)phenyl]benzimidazole oxalate was prepared from 1-(2-amino-1-benzimidazolyl)-3-iodobenzene and 2-trimethylstannylfuran according to method C. mp 131°–133° C.

EXAMPLE 11

2-Amino-1-[4-(2-furyl)phenyl]benzimidazole was prepared from 1-(2-amino-1-benzimidazolyl)-4-iodobenzene and 2-trimethylstannylfuran according to method C, mp 210°–212° C.

EXAMPLE 12

2-Amino-1-[3-(2-thienyl)phenyl]benzimidazole was prepared from 1-(2-amino-1-benzimidazolyl)-3-iodobenzene and 2-thienylboronic acid by method B. mp 142°–144° C.

EXAMPLE 13

2-Amino-1-[3-(3-methoxymethyl-2-furyl)phenyl]benzimidazole was prepared from 1-(2-amino-1-benzimidazolyl)-3-iodobenzene and 3-methoxymethyl-2-trimethylstannylfuran by method C. mp 134°–136° C.

EXAMPLE 14

2-Amino-1-[3-(1,3,5-trimethyl-4-pyrazolyl)phenyl]benzimidazole was prepared from 3-(2-amino-1-benzimidazolyl)-phenyl-1,3,2-dioxaborinane and 4-bromo-1,3,5-trimethylpyrazole by method A. mp 198°–200° C.

EXAMPLE 15

2-Amino-1-[3-(3-methoxymetyl-2-furyl)-4-methylphenyl]benzimidazole was prepared from 4-(2-amino-1-benzimidazolyl)-2-iodotoluene and 3-methoxymethyl-2-trimethylstannylfuran according to method C. mp 174°–176° C.

EXAMPLE 16

2-Amino-1-[3-(2-furyl)-4-methylphenyl]benzimidazole was prepared from 4-(2-amino-1-benzimidazolyl)-2-iodotoluene and 2-trimethylstannylfuran according to method C. mp 155°–157° C.

EXAMPLE 17

1-(2-Amino-1-benzimidazolyl)-3-(1-benzimidazolyl)-benzene hydrochloride was prepared from 1-(2-amino-1-benzimidazolyl)-3-N-(2-aminophenyl)aniline by refluxing with 25% aqueous hydrochloric acid and formic acid (2:1). mp 210°–212° C.

EXAMPLE 18

2-Amino-1-[3-(5-acetamido-1-methyl-4-pyrazolyl)-phenyl]benzimidazole was prepared from 3-(2-amino-1-benzimidazolyl)-phenyl-1,3,2-dioxaborinane and 3-acetamido-4-bromo-2-methylpyrazole according to method A. mp 135°–137° C.

EXAMPLE 19

2-Amino-1-[3-(5-amino-1-methyl-4-pyrazolyl)-phenyl]benzimidazole hydrochloride was prepared from 2-amino-1-[3-(5-acetamido-1-methyl-4-pyrazolyl)-phenyl]benzimidazole by hydrolysis with 25% refluxing hydrochloric acid. mp 190°–193° C.

EXAMPLE 20

2-Amino-1-[3-(3-furyl)-4-cyanophenyl]benzimidazole was prepared from 2-amino-1-[3-chloro-4-cyanophenyl]benzimidazole and 3-furylboronic acid by method B. mp 140°–144° C.

EXAMPLE 21

2-Amino-1-[3-(2-furyl)-4-methoxyphenyl]benzimidazole was prepared from 4-N-(2-aminophenyl)amino-2-(2-furyl)anisole by method D. mp 218°–221° C.

EXAMPLE 22

2-Amino-1-[3-(2-furyl)-4-dimethylaminophenyl]benzimidazole was prepared from 4-N'-(2-aminophenyl)amino-N,N-dimethyl-2-(2-furyl)aniline according to method D. mp 208°–210° C.

EXAMPLE 23

2-Amino-1-[3-(5-[2H-1,3-benzodioxol])phenyl]benzimidazole was prepared from 3-(2-amino-1-benzimidazolyl)-phenyl-1,3,2-dioxaborinane and 5-bromo-1,3-benzo-dioxol according to method A. mp 111°–113° C.

EXAMPLE 24

2-Amino-1-[3-(5-indolyl)phenyl]benzimidazole was prepared from 3-(2-amino-1-benzimidazolyl)-phenyl-1,3,2-dioxaborinane and 5-bromoindole according to method A. mp 120°–123° C.

EXAMPLE 25

1,3-Bis(2-amino-1-benzimidazolyl)benzene (mp 270°–275° C.) and 1-(2-amino-1-benzimidazolyl)-3-N-(2-aminophenyl)aniline (mp 85°–87° C.) was prepared from N,N'-bis(2-aminophenyl)-meta-phenylenediamine by reaction with 1.5 equivalents of cyanogen bromide with DMF as the reaction solvent. After extractive workup as in method D, the products were separated by column chromatography on silica gel with dichloromethane containing 10% ethanol as the eluent, 1,3-Bis(2-amino-1-benzimidazolyl)benzene being the more polar component.

Intermediates 1-(2-Amino-5-trifluoromethyl-1-benzimidazolyl)-3-iodobenzene was prepared from N-(3-iodophenyl)-4-trifluoromethyl-ortho-phenylenediamine according to method D. mp 208°–210° C.

N-(3-iodophenyl)-4-trifluoromethyl-ortho-phenylenediamine (mp 184°–186° C., as hydrochloride)

was prepared in the same manner as 2-amino-3'-iododiphenylamine.

2-Thienylboronic acid was prepared according to the literature (A. -B. Hörnfeldt and S. Gronowitz, Arkiv för Kerni, 21, 239 (1963)).

2-Trimethylstannylthiazole was prepared according to the literature (C. Jutz, S. M. Wagner, A. Kraatz, and H. G. Löberling, Liebigs Ann. Chem. 5, 874 (1975)).

2-Furylboronic acid and 3-furylboronic acid was prepared according to the literature (B. P. Roques, D. Florentin, and M. Callanquin, J. Hetererocycl. Chem., 122, 195 (1963)).

N-Phenylbenzyl-4-trifluoromethyl-ortho-phenylenediamine was prepared by hydrogenation in the same way as 2-amino-3'-(1,3,2-dioxaborinanyl) diphenylamine.

2-Trimethylstannylfuran. To a stirred solution of furan (17.1 g, 251 mmol) in dry ether (300 ml) under nitrogen was added 2M butyllithium in cyclohexane (138 ml) at such a rate that the mixture refluxed gently. After 30 minutes the temperature was lowered to −60° C. and a solution of trimethylstannyl chloride (50 g, 251 mmol) in THF (50 ml) was added during 2 h. The cooling bath was removed and the mixture was allowed to stir overnight. Water (250 ml) was added and the phases were separated. The aqueous phase was extracted with ether (3×120 ml) and the combined ethereal phases were dried over magnesium sulphate and the solvent was evaporated. The crude product was purified by distillation at 50°–53° at 15 Torr. Yield 37.6 g, 68%.

3-Methoxymethyl-2-trimethylstannylfuran was prepared in the same manner as 2-trimethylstannylfuran with 3-methoxymethylfuran as starting material. bp 93°–97° C. at 15 Torr.

1-(2-Amino-1-benzimidazolyl)-4-iodobenzene (mp 212°–214° C.) was prepared from 4-iodoaniline via 4-iodo-2'-nitrodiphenylamine (mp 174°–175° C.) and 4-iodo-2'-aminodiphenylamine (mp 127°–128° C.), in analogy with the sequence used in the preparation of 1-(2-amino-1-benzimidazolyl)-3-iodobenzene.

3-acetamido-4-bromo-2-methylpyrazole (92°–94° C.) was prepared by acetylation of 3-amino-4-bromo-2-methylpyrazole in acetic anhydride.

2-Amino-1-[3-chloro-4-cyanophenyl]benzimidazole was prepared according to the sequence: Reaction between 2-fluoro-1-nitrobenzene and 3-chloro-4-cyanoaniline (see preparation of 3-iodo-2'-nitro-diphenylamine) gave 3-chloro-4-cyano-2'-nitrodiphenylamine (mp 165°–167° C.), which was converted to 2-amino-3'-chloro-4'-cyan o-diphenylamine (mp 230°–234° C., as the hydrochloride) by reduction with sulfide (see preparation of 2-amino-3'-iododiphenylamine), which then was treated according to method D to yield 2-amino-1-[3-chloro-4-cyanophenyl]benzimidazole (mp 245°–248° C.).

4-N-(2-Aminophenyl)amino-2-(2-furyl)anisole (oil) was prepared according to the following sequence: The palladium catalyzed coupling of 2-bromo-4-nitroanisole and 2-trimethylstannylfuran (see method C) gave 2-(2-furyl)-4-nitroanisole (mp 18°–120° C.) which was then subjected to catalytic hydrogenation (see preparation of amino-3'-(1,3,2-dioxaborinanyl)diphenylamine) to yield 3-(2-furyl)-4-methoxyaniline (oil). This compound was allowed to react with 1-fluoro-2-nitrobenzene (see preparation of 3-iodo-2'-nitro-diphenylamine) to yield 4-N-(2-nitrophenyl)amino-2 -(2-furyl)anisole (mp 130°–132° C.) which after hydrogenation (see preparation of amino-3'-(1,3,2-dioxaborinanyl)diphenylamine) gave 4-N-(2-aminophenyl) amino-2-(2-furyl)anisole.

4-N'-(2-Aminophenyl)amino-N,N-dimethyl-2-(2-furyl)aniline was prepared according to the following sequence: The palladium catalyzed coupling of 3-chloro-4-fluoronitrobenzene and 2-furylboronic acid (see method B) gave 4-fluoro-3-(2-furyl)nitrobenzene (mp 110°–112° C.) which after treatment with dimethylamine yielded 4-N,N-dimethylamino-3-(2-furyl)nitrobenzene as a yellow oil. This compound was hydrogenated (see preparation of amino-3'-(1,3,2-dioxaborinanyl)diphenylamine) and the product, 4-N,N-dimethylamino-3-(2-furyl)aniline, was obtained as an oil. After reaction with 1-fluoro-2-nitrobenzene (see preparation of 3-iodo-2'-nitro-diphenylamine) the yellow compound 4-N'-(2-aminophenyl)amino-N,N-dimethyl-2-(2-furyl)nitrobenzene (mp 124°–126° C.) was obtained, which after hydrogenation yielded 4-N'-(2-aminophenyl)amino-N,N-dimethyl-2-(2-furyl) aniline as an oil.

4-Hydroxymethyl-3-thienylboronic acid. To a solution of 4-formyl-3-thienylboronic acid (1.0 g, 6.4 mmol) in dry THF (10 ml) sodium borohydride (0.27 g, 7.1 mmol) was added. The mixture was stirred at room temperature for 30 minutes. The reaction was then stopped by the addition of 1M hydrochloric acid and was then extracted with ethyl acetate, dried and evaporated to dryness. Yield: 0.9 g, 89%, dec. at ≈120° C.

4-Formyl-3-thienyl boronic acid was prepared according to the literature (S. Gronowitz and V. Michael-/Acta Chem. Scand. 22, 1353 (1968)).

3-(2-Amino-1-benzimidazolyl)-phenyl-1,3,2-dioxaborinane. A mixture of 2-amino-3'-(1,3,2-dioxaborinanyl)diphenylamine (26.0 g, 97.0 mmol), cyanogen bromide (15.4 g, 145 mmol) and DMF (200 ml) was stirred in a sealed bottle in the absence of light for 15 h. Water (400 ml) was added and the resulting mixture was neutralized with sodium hydroxide (4M). The mixture was filtered and the solid residue was washed with methanol and was found to be 3-(2-amino-1-benzimidazolyl)-phenylboronic acid (Yield 5.0 g, 20%, mp. 240°–245° C.). The filtrate was evaporated to dryness at a pressure of 1 Torr. Water (200 ml) was added and the product was collected by filtration. Yield: 15.0 g, 53%, mp. 150°–155° C.

2-Amino-3'-(1,3,2-dioxaborinanyl)diphenylamine. A mixture of 3'-(1,3,2-dioxaborinanyl)-2-nitrodiphenylamine (30.9 g, 104 mmol) and 5% palladium on charcoal (3.1 g) in methanol (300 ml) was hydrogenated at ambient pressure until three. equivalents of hydrogen gas had been taken up. The reaction mixture was filtered through a celite pad and the solvent was evaporated. Yield: 26.5 g, 95%, top. 220°–222° C. (for the hydrochloride).

3'-(1,3,2-Dioxaborinanyl)-2-nitrodiphenylamine. A mixture of 2-nitro-diphenylamine-3'-boronic acid (27 g, 105 mmol), 1,3-propanediol (9.55 g, 126 mmol), and toluene (500 ml) was refluxed for 2 h with a Dean-Stark water separator attached. The solvent was evaporated and the product was obtained as a yellow oil. Yield: 31 g, 99% (The product still contained some 1,3-propanediol).

2-Nitro-diphenylamine-3'-boronic acid. A mixture of 2-fluoronitrobenzene (37.9 g, 268 mmol), 3-aminophenylboronic acid hemisulfate (50 g, 268 mmol), and dry potassium carbonate (59.3 g, 429 mmol) in DMF (200 ml) was heated to 90'C under nitrogen for 40 h. The crude product was dissolved in ether (500 ml) and washed twice with 1M aqueous hydrochloric acid (200 ml). After purification by filtration through a short column of silica gel, the product was obtained as a yellow solid. Yield: 27.2 g, 39%, mp 195°–196° C.

2-Amino-3'-iododiphenylamine. A mixture of 3-iodo-2'-nitro-diphenylamine. (69.4 g, 204 mmol), and Na$_2$S.9 H$_2$O (245 g, 1.02 mol), ammonium chloride (54.6 g, 1.02 mol) in ethanol (600 ml) was refluxed under nitrogen for 3 h. The solvent was removed by evaporation and water (350 ml) was added whereupon the suspended product was collected by filtration. Yield: 62.6 g, 99%, mp 90°–94° C.

3-Iodo-2'-nitro-diphenylamine. A mixture of 2-fluoronitrobenzene (77.3 g, 548 mmol), 3-iodoaniline (100 g, 457 mmol), and dry potassium carbonate (75.7 g, 548 mmol) was heated to 180° C. under nitrogen for 1 week. The crude product was dissolved in a mixture of ether and water. The phases were separated and the aqueous phase was extracted with another portion of ether. The combined ethereal phases were dried over magnesium sulfate and evaporated to dryness. Yield: 74.5 g, 48%, mp 89°–91° C.

3-Chloro-4-methoxy-1,2,5-thiadiazole. Sodium (0.71 g, 31.0 mmol) was added to dry methanol (20 ml). After the metal had dissolved, dichloro-1,2,5-thiadiazole (4.0 g, 25.8 mmol) was added and the reaction mixture was then stirred for 15 min. Water and ether was added and the phases were separated. Traces of 3-Chloro-4-methoxy-1,2,5-thiadiazole was removed by chromatography on silica gel with petroleum ether as eluent. The product still contained some 20% dimethoxy-1,2,5thiadiazole but since it was of no consequence for the next step, the product was not further purified.

We claim:

1. A method of treating a disorder, which is responsive to the partial or complete blockade of calcium channels of the central nervous system of a living animal body, which comprises administering to a living animal body in need thereof, a therapeutically-effective amount of a compound selected from those having the formula:

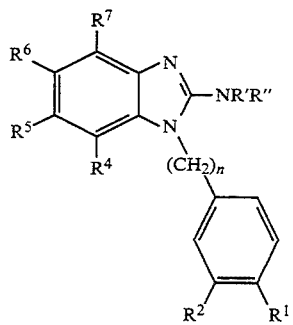

or a pharmaceutically-acceptable addition salt thereof, wherein R' and R" independently of each other are hydrogen or C$_{1-6}$-alkyl, or R' and R" together form a 3 to 6 membered alkylene chain; one of R$^1$ and R$^2$ is phenyl, oxazolyl, isoxazolyl, thiazolyl, isothiazolyl, oxadiazolyl, thiadiazolyl, imidazolyl, pyrrolyl, furyl, thienyl, pyridyl, benzimidazolyl, indolyl, pyrazolyl, or benzodioxolyl, all of which may be substituted one or more times with halogen, CF$_3$, CN, OH, C$_{1-6}$-alkyl, C$_{3-7}$-cycloalkyl-C$_{1-6}$-alkyl, C$_{2-6}$-alkenyl, C$_{2-6}$-alkynyl, C$_{1-6}$-alkoxy, amino, nitro, sulphamoyl, tetrazolyl, CO$_2$H, or CO$_2$-C$_{1-6}$-alkyl and the other of R$^1$ and R$^2$ is hydrogen, halogen, C$_{1-6}$-alkoxy, amino, or C$_{1-6}$-alkyl; and R$^4$, R$^5$, R$^6$, and R$^7$ independently of each other are hydrogen, halogen, amino, nitro, CN, OH, CF$_3$, C$_{1-6}$-alkyl, or C$_{1-6}$-alkoxy; and n is 0 or 1; provided that neither of R$^1$ and R$^2$ is phenyl or substituted phenyl when n is 0.

2. A method as in claim 1, wherein stroke, anoxia, ischemia, migraine, or epilepsy is treated.

3. A method as in claim 1, wherein Parkinsonism, epilepsy or any other convulsive disorder is treated.

4. A method of claim 1, wherein the compound employed is

2-Amino-1-[3-(4-methoxy-1,2,5-thiadiazol-3-yl)-phenyl]-benzimidazole, 1,3-bis(2-amino-1-benzimidazolyl)benzene, 2-Amino-1-[3-(3-formyl-4-thienyl)-phenyl]-benzimidazole, 2-Amino-1-[3-(3-hydroxymethyl-4-thienyl)-phenyl]-benzimidazole, 2-Amino-1-[3(2-thiazolyl)phenyl]benzimidazole, 2-Amino-1-[3(2-thienyl)phenyl]-5-trifluoromethyl-benzimidazole, 2-Amino-1-(4-phenylbenzyl)-5-trifluoromethylbenzimidazole, 2-Amino-1-[6-(2-hydroxypyridyl)phenyl]benzimidazole hydrochloride, 2-Amino-1-[3(thiazolyl)phenyl]benzimidazole, 2-Amino-1-[3-(2-furyl)phenyl]benzimidazole oxalate, 2-Amino-1-[4-(2-furyl)phenyl]benzimidazole, 2-Amino-1-[3-(2-thienyl)phenyl]benzimidazole, 2-Amino-1-[3-(3-methoxymethyl-2-furyl)phenyl]benzimidazole, 2-Amino-1-[3-(1,3,5-trimethyl-4-pyrazolyl)phenyl]-benzimidazole, 2-Amino-1-[3-(3-methoxymethyl-2-furyl)-4-methyl-phenyl]benzimidazole, 2-Amino-1-[3-(2-furyl)-4-methylphenyl]benzimidazole, 1-(2-Amino-1-benzimidazolyl)-3-(1-benzimidazolyl)-benzene hydrochloride, 2-Amino-1-[3-(5-acetamido-1-methyl-4-pyrazolyl)-phenyl]benzimidazole, 2-Amino-1-[3-(5-amino-1-methyl-4-pyrazolyl)-phenyl]benzimidazole hydrochloride, 2-Amino-1-[3-(3-furyl)-4-cyanophenyl]benzimidazole, 2-Amino-1-[3-(2-furyl)-4-methoxyphenyl]benzimidazole, 2-Amino-1-[3-(2-furyl)-4-dimethylaminophenyl]benzimidazole, 2-Amino-1-[3-(5-[2H-1,3-benzodioxol])phenyl]benzimidazole, 2-Amino-1-[3-(5-indolyl)phenyl]benzimidazole, or 1,3-Bis(2-amino-1-benzimidazolyl)benzene, or another pharmaceutically-acceptable addition salt thereof.

5. The method of claim 1, wherein the active ingredient is administered in the form of a pharmaceutical composition thereof, in which it is present together with a pharmaceutically-acceptable carrier of diluent.

6. A method of preventing the neurotoxic degenerative changes connected with stroke, anoxia, ischemia, migraine, Parkinsonism, epilepsy or any other convulsive disorder, which comprises administering to a living animal body in need thereof a therapeutically-effective amount of a compound of claim 1.

7. A method of claim 1, wherein the compound administered is 2-Amino-1-[3-(4-methoxy-1,2,5-thiadiazol-3-yl)-phenyl]-benzimidazole, or a pharmaceutically-acceptable addition salt thereof.

8. A compound having the formula

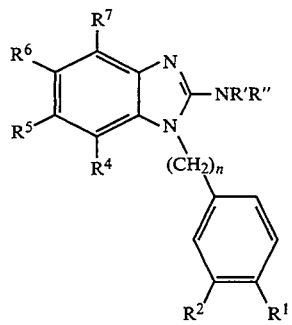

or a pharmaceutically-acceptable addition salt thereof, wherein R' and R'' independently of each other are hydrogen or $C_{1-6}$-alkyl, or R' and R'' together form a 3 to 6 membered alkylene chain; one of $R^1$ and $R^2$ is oxazolyl, isoxazolyl, thiazolyl, isothiazolyl, oxadiazolyl, thiadiazolyl, imidazolyl, pyrrolyl, furyl, thienyl, pyridyl, benzimidazolyl, indolyl, pyrazolyl, or benzodioxolyl, all of which may be substituted one or more times with halogen, $CF_3$, CN, OH, $C_{1-6}$-alkyl, $C_{3-7}$-cycloalkyl-$C_{1-6}$-alkyl, $C_{2-6}$-alkenyl, $C_{2-6}$-alkynyl, $C_{1-6}$-alkoxy, amino, nitro, sulphamoyl, tetrazolyl, $CO_2H$, or $CO_2$-$C_{1-6}$-alkyl, OR one of $R^1$ and $R^2$ is phenyl which may be substituted one or more times with halogen, $CF_3$, OH, $C_{1-6}$-alkyl, $C_{3-7}$-cycloalkyl-$C_{1-6}$-alkyl, $C_{2-6}$-alkenyl, $C_{2-6}$-alkynyl, $C_{1-6}$-alkoxy, or nitro, and the other of $R^1$ and $R^2$ in any case is hydrogen, halogen, $C_{1-6}$-alkoxy, amino, or $C_{1-6}$-alkyl; and $R^4$, $R^5$, $R^6$, and $R^7$ independently of each other are hydrogen, halogen, amino, nitro, CN, OH, $CF_3$, $C_{1-6}$-alkyl, or $C_{1-6}$-alkoxy; and n is 0 or 1; provided that neither of $R^1$ and $R^2$ is phenyl or substituted phenyl when n is 0.

9. A compound of claim 8 which is
2-Amino-1-[3-(4-methoxy-1,2,5-thiadiazol-3-yl)-phenyl]-benzimidazole,
1,3-bis(2-amino-1-benzimidazolyl)benzene,
2-Amino-1-[3-(3-formyl-4-thienyl)-phenyl]-benzimidazole,
2-Amino-1-[3-(3-hydroxymethyl-4-thienyl)-phenyl]-benzimidazole,
2-Amino-1-[3(2-thiazolyl)phenyl]benzimidazole,
2-Amino-1-[3(2-thienyl)phenyl]-5-trifluoromethyl-benzimidazole,
2-Amino-1-(4-phenylbenzyl)-5-trifluoromethylbenzimidazole,
2-Amino-1-[6-(2-hydroxypyridyl)phenyl]benzimidazole hydrochloride,
2-Amino-1-[3(2-thiazolyl)phenyl]benzimidazole,
2-Amino-1-[3-(2-furyl)phenyl]benzimidazole oxalate,
2-Amino-1-[4-(2-furyl)phenyl]benzimidazole,
2-Amino-1-[3-(2-thienyl)phenyl]benzimidazole,
2-Amino-1-[3-(3-methoxymethyl-2-furyl)phenyl]benzimidazole,
2-Amino-1-[3-(1,3,5-trimethyl-4-pyrazolyl)phenyl]-benzimidazole,
2-Amino-1-[3-(3-methoxymethyl-2-furyl)-4-methylphenyl]benzimidazole,
2-Amino-1-[3-(2-furyl)-4-methylphenyl]benzimidazole,
1-(2-Amino-1-benzimidazolyl)-3-(1-benzimidazolyl)-benzene hydrochloride,
2-Amino-1-[3-(5-acetamido-1-methyl-4-pyrazolyl)-phenyl]benzimidazole,
2-Amino-1-[3-(5-amino-1-methyl-4-pyrazolyl)-phenyl]benzimidazole hydrochloride,
2-Amino-1-[3-(3-furyl)-4-cyanophenyl]benzimidazole,
2-Amino-1-[3-(2-furyl)-4-methoxyphenyl]benzimidazole,
2-Amino-1-[3-(2-furyl)-4-dimethylaminophenyl]benzimidazole,
2-Amino-1-[3-(5-[2H-1,3-benzodioxol])phenyl]benzimidazole,
2-Amino-1-[3-(5-indolyl)phenyl]benzimidazole, or
1,3-Bis(2-amino-1-benzimidazolyl)benzene,
or another pharmaceutically-acceptable addition salt thereof.

10. A compound of claim 8 which is 2-Amino-1-[3-(4-methoxy-1,2,-thiadiazol-3-yl)-phenyl]-benzimidazole, or a pharmaceutically-acceptable addition salt thereof.

11. A pharmaceutical composition comprising an effective amount of a compound of claim 7, together with at least one pharmaceutically-acceptable carrier or diluent.

12. A pharmaceutical composition useful for the partial or complete blockade of calcium channels of the central nervous system of a living animal body, which comprises a therapeutically-effective amount of a compound selected from the following compounds:
2-Amino-1-[3-(4-methoxy-1,2,5-thiadiazol-3-yl)-phenyl]-benzimidazole,
1,3-bis(2-amino-1-benzimidazolyl)benzene,
2-Amino-1-[3-(3-formyl-4-thienyl)-phenyl]-benzimidazole,
2-Amino-1-[3-(3-hydroxymethyl-4-thienyl)-phenyl]-benzimidazole,
2-Amino-1-[3(2-thiazolyl)phenyl]benzimidazole,
2-Amino-1-[3(2-thienyl)phenyl]-5-trifluoromethyl-benzimidazole,
2-Amino-1-(4-phenylbenzyl)-5-trifluoromethylbenzimidazole,
2-Amino-1-[6-(2-hydroxypyridyl)phenyl]benzimidazole hydrochloride,
2-Amino-1-[3(2-thiazolyl)phenyl]benzimidazole,
2-Amino-1-[3-(2-furyl)phenyl]benzimidazole oxalate,
2-Amino-1-[4-(2-furyl)phenyl]benzimidazole,
2-Amino-1-[3-(2-thienyl)phenyl]benzimidazole,
2-Amino-1-[3-(3-methoxymethyl-2-furyl)phenyl]benzimidazole,
2-Amino-1-[3-(1,3,5-trimethyl-4-pyrazolyl)phenyl]-benzimidazole,
2-Amino-1-[3-(3-methoxymethyl-2-furyl)-4-methylphenyl]benzimidazole,
2-Amino-1-[3-(2-furyl)-4-methylphenyl]benzimidazole,
1-(2-Amino-1-benzimidazolyl)-3-(1-benzimidazolyl)-benzene hydrochloride,
2-Amino-1-[3-(5-acetamido-1-methyl-4-pyrazolyl)-Phenyl]benzimidazole,
2-Amino-1-[3-(5-amino-1-methyl-4-pyrazolyl)-phenyl]benzimidazole hydrochloride,
2-Amino-1-[3-(3-furyl)-4-cyanophenyl]benzimidazole,
2-Amino-1-[3-(2-furyl)-4-methoxyphenyl]benzimidazole, 2-Amino-1-[3-(2-furyl)-4-dimethylaminophenyl]benzimidazole,
2-Amino-1-[3-(5-[2H-1,3-benzodioxol])phenyl]benzimidazole,
2-Amino-1-[3-(5-indolyl)phenyl]benzimidazole, or 1,3-Bis(2-amino-1-benzimidazolyl)benzene,
or a or another pharmaceutically-acceptable addition salt thereof, together with at least one pharmaceutically-acceptable carrier or diluent.

* * * * *

UNITED STATES PATENT AND TRADEMARK OFFICE
CERTIFICATE OF CORRECTION

PATENT NO. : 5,441,969
DATED : August 15, 1995
INVENTOR(S) : Oskar Axelsson; Dan Peters, Elsebet O. Nielsen Page 1 of 3

It is certified that error appears in the above-indentified patent and that said Letters Patent is hereby corrected as shown below:

Col. 2, line 63: "[3-   (2-furyl)" should read -- [3-(2-furyl) --.

Col. 4, line 13: "[3-   (2-furyl)-" should read -- [3-(2-furyl)- --.

Col. 4, line 27: "[2H-   1,3-benzodioxol])" should read -- [2H-1,3-benzodioxol]) --.

Col. 4, line 66: "1,2,5-oxadiazol3-yl," should read -- 1,2,5-oxadiazol-3-yl, --.

Col. 5, line 68: "Substitution" should read -- substitution --.

Col. 7, line 37: "synaptosornes" should read -- synaptosomes --

Col. 8, line 4: "45CACl$_2$" should read -- $^{45}$CaCl$_2$" --

Col. 8, line 6: "$^{45}$CACl$_2$" should read -- $^{45}$CaCl$_2$ --

Col. 10, line 29: "sollubilizing" should read -- solubilizing"

UNITED STATES PATENT AND TRADEMARK OFFICE
CERTIFICATE OF CORRECTION

PATENT NO. : 5,441,969
DATED : August 15, 1995
INVENTOR(S) : Oskar Axelsson; Dan Peters, Elsebet O. Nielsen It is certified that error appears in the above-indentified patent and that said Letters Patent is hereby corrected as shown below:

Col. 12, line 26: "Starting" should read -- starting --

Col. 12, line 65: "2-Amino-1-]" should read -- 2-Amino-1-[ --

Col. 13, line 3: "2-Amine" should read -- 2-Amino --

Col. 14, line 26: Add ")" to end of line before the dash (-)

Col. 14, line 27: Delete ")" at beginning of the line.

Col. 14, line 33: Add ")" to end of line before the dash (-).

Col. 14, line 33: Delete ")" at beginning of the line.

Col. 14, line 51: "270° 275°C)" should read -- 270-275°C) --.

Col. 15, line 5: "Kerni" should read -- Kemi --.

Col. 15, line 61: "(mp 18°-120°C)" should read -- (mp 118-120°C) --

UNITED STATES PATENT AND TRADEMARK OFFICE
CERTIFICATE OF CORRECTION

PATENT NO. : 5,441,969
DATED : August 15, 1995
INVENTOR(S) : Oskar Axelsson; Dan Peters, Elsebet O. Nielsen It is certified that error appears in the above-indentified patent and that said Letters Patent is hereby corrected as shown below:

Col. 16, line 50: "three." should read -- three --

Col. 17, line 32 (approx.): "1,2,5thiadiazole" should read -- 1,2,5-thiadiazole --.

Col. 18, line 39: "[3-    (2-furyl)" should read -- [3-(2-furyl) --.

Col. 20, line 1: "[3-    (2-furyl)" should read -- [3-(2-furyl) --.

Col. 20, line 62: "Phenyl]" should read -- phenyl] --.

Signed and Sealed this

Twenty-eighth Day of November 1995

Attest:

BRUCE LEHMAN

*Attesting Officer*     *Commissioner of Patents and Trademarks*